United States Patent [19]

Moallemi

[11] Patent Number: 5,744,662
[45] Date of Patent: Apr. 28, 1998

[54] SEPARATION OF R-12 AND R-134A BY A LIQUID-LIQUID EXTRACTION TECHNIQUE

[76] Inventor: Mohamad Karim Moallemi, 76-16 Grand Central Pkwy, π1A, Forest Hills, N.Y. 11375

[21] Appl. No.: 635,439

[22] Filed: Apr. 17, 1996

[51] Int. Cl.$^6$ .................................................. C07C 17/38
[52] U.S. Cl. ............................................................. 570/180
[58] Field of Search ........................................... 570/180

[56] References Cited

U.S. PATENT DOCUMENTS 5,087,329  2/1992  Felix.
5,099,082  3/1992  Bolmer.

Primary Examiner—Alan Siegel

[57] ABSTRACT

A process for separating and purifying dichlorodifluoromethane and 1,1,1,2 tetrafluoroethane from a feed of their mixtures by liquid-liquid extraction with extracting solvent containing paraffinic or naphthalenic mineral oils or a mixture thereof, with or without a stripping agent such as ethylene glycol or triethylene glycol or a mixture thereof.

11 Claims, 6 Drawing Sheets

SEPARATION OF R-12 AND R-134A BY A LIQUID-LIQUID EXTRACTION TECHNIQUE

FIELD OF THE INVENTION

This invention relates to a process for separating hydrofluorocarbons (HFC's) in a mixture of chlorofluorocarbons (CFC's) and hydrochlorofluorocarbons (HCFC's) by extracting the hydrofluorocarbon by a liquid-liquid extraction using a mineral oil.

BACKGROUND OF THE INVENTION

Chlorofluorocarbons (CFC's) are well-recognized ozone depleting substances that have been traditionally used as a refrigerant in vapor compression refrigeration systems, and have also been used as blowing and cleaning agents. In Copenhagen, in November 1992, the international community, including the United States, under the auspices of the United Nations reached to a consensus with other nations for a schedule that will phase-out the production of CFC's and HCFC's. The productions of the CFC's are banned now, and the phase-out of HCFC production will be completed by 2005.

As part of the Clean Air act of 1990, it is illegal to intentionally vent into the atmosphere any CFC or HCFC refrigerants in the course of performing refrigeration service work. Moreover, beginning on Jul. 1, 1992, the Environmental Protection Agency mandated that all CFC and HCFC refrigerants were to be removed and recovered from retiring systems. The recovered CFC and HCFC refrigerants must be purified (reclaimed) before resale for use in the existing systems. In the event that recovered refrigerants are contaminated beyond reclamation, they must be converted to environmentally benign substances via incineration or other means.

In the view of the production phase-out of CFC and HCFC refrigerants, 1,1,1,2 tertrafluoroethane (a HFC compound, a.k.a R-134a) has been introduced as an environmentally benign replacement for dichlorodifluoromethane (R-12) as well as chlorodifluoromethane (a HCFC compound, a.k.a R-22) in some systems. R-134a has gained acceptance by the "Original Equipment Manufacturers" in the automotive and appliance's industries, as well as the repair and maintenance trades. However, refrigerants R-12 and R-134a are different and their mixing in a vapor compression system will result in significant deterioration in the performance of the system. R-134a also has a limited solubility in the mineral oils that are used in the compressors with old refrigerants (R-12 and R-22). Therefore, retrofitting of the existing systems for use of R-134a involves total recovery and removal of the old refrigerant (R-12 or R-22) and complete removal of the mineral oil before the substitution of the new refrigerant (R-134a) and the new ester-based oils.

The mixing of the refrigerants may occur during flashing and recharging of a system that is repaired or retrofitted (by mistake or negligence of the technicians). The refrigerants may also become mixed when the refrigerant is recovered from a system prior to its retirement or repair. Different refrigerant components in mixtures have to be separated during the reclamation process where used refrigerant (removed from systems) is purified to the accepted purity standard set by American Refrigeration Institute (ARI-700 standard) for resale and reuse. The alternate approach is chemical distraction of the mixtures or contaminated batches. This is costly and the valuable refrigerant components are rendered worthless by chemical conversion to environmentally benign products that may be released into biosphere.

Therefore, there is a need for a process for separating old refrigerants (R-12 and R-22) from their mixtures with their replacements R-134a). Separation by conventional distillation methods is extremely difficult and not economically feasible because the small difference between the boiling points of these refrigerants.

It is therefore desirable to have an efficient and cost effective process for separating R-134a refrigerant from its mixtures with R-12 and R-22 in liquid phase.

It is also desirable if an indirect separation technique could be used that involves two immiscible liquid phases and introduces a foreign substance (referred to as extraction solvent). This process could provide a very high separation efficiency with an appropriately selected extraction solvent. This process would not destroy the valuable refrigerant components in the mixture. Moreover, it would not generate a waste stream because the extraction solvent (and the stripping agent, if used) would be reused in the process after recovery of the solute (one of the feed mixture components) via boil-off or simple distillation.

DESCRIPTION OF THE PRIOR ART

Liquid-liquid extraction is an energy efficient and cost effective separation process as compared with direct separation techniques (e.g., distillation) where vapor phase is produced by heating, or melt crystallization, where cooling is used to provide a solid phase. Liquid-liquid extraction technique is particularly superior to direct distillation where the mixture components have close boiling points and effective separation is not possible or practical by distillation because a large number of stages would be required. Liquid-liquid extraction technique, though widely used in many applications, has not been applied to the separation of R-134a from its mixtures with R-12 or R-22. Various applications of liquid-liquid extraction have been reported for the separation of different mixtures of various chlorofluorohydrocarbons. Examples include:

U.S. Pat. No. 5,087,329 discloses a process for separating pentafluoroethane (R-125) from its mixture with chloropentafluoroethane (R-115) by extractive distillation by adding a fluorocarbon extractive agent having 1–4 carbon atoms (e.g. R-11, R-113, R-123).

U.S. Pat. No. 5,099,082 discloses a process for separating a mixture of 1,1,1,3,3-pentafluorobutane (R-365) and 1,1-dichloro-1-fluoroethane (R-141b) by liquid-liquid extraction with solvents containing ethylene glycol, and other solvents.

U.S. Pat. No. 3,840,607 discloses a process for separating halogenated hydrocarbons, such as 1,1,2-trichlorotrifluoroethane (R-113), and 1,2dichloro-1,1difluoroethane (R-132b) using sulfolane as the extracting solvent.

U.S. Pat. No. 4,031,148 discloses a process for separating $C_1$ and $C_3$ chlorinated aliphatic hydrocarbons from their mixtures in the presence of extraction agent(s) selected from the group of aprotic polar solvents.

U.S. Pat. No. 5,189,230 discloses a process for separating olefins (R-1326 and R-1122 particularly) from chlorofluorohydrocarbons in the presence of oxygen-containing phase transfer catalysts with complex hydrides or strong bases (LIH, KOH, $NaBH_4$).

U.S. Pat. No. 5,208,398 discloses a process for separating of R-365 and R-141b by liquid-liquid extraction with HF as the extraction agent.

None of these references involves mixtures of R-134a with R-12 or R-22, nor does the references have paraffinic and/or naphthalenic mineral oils used in previous art as the extraction solvent for the separation of HFC's from their mixtures with HCFC's and CFC's. The applicant is not aware of literature that discloses a liquid-liquid extraction for separating R-134a from R-12 or R-22. Also, as noted in U.S. Pat. Nos. 4,031,148 and 5,099,082, it is impossible to foresee which extraction agent will render the separation of any two substances feasible.

The conventional fractional distillation may not be employed to separate R-134a from R-12 (and R-22) effectively (e.g., resulting in the separation of a substantially pure component at one end of the column) because the boiling points are close and the relative volatility of the compounds are low. Experiments on R-134a mixtures with R-12 (and R-22), used the PTx method to determine the relative volatility of these mixtures. The relative volatility of R-12 in R-134a changes from 0.8 to 1.2 as the concentration of R-12 is decreased in the mixture. This makes the separation of a substantially pure component at one end of the column most difficult, if not impossible. For the case of mixtures with R-22, the relative volatility of R-22 in R-134a changes from 1.4 to 1.5 with reducing concentration of R-22 in the mixture. The separation of this mixture by distillation is more feasible in the previous case, but as will be shown, the liquid-liquid extraction is more effective and efficient for both mixtures.

SUMMARY OF THE INVENTION

The present invention provides a method for partial or total separation of R-134a from its mixtures with R-12 and/or R-22 comprising liquid-liquid extraction on the mixture in the presence of an extraction solvent containing paraffinic and/or naphthalenic mineral oils, or a mixture thereof, with or without a stripping agent such as ethylene glycol or triethylene glycol. More specifically, the process comprises contacting the mixtures of R-134a and R-12 (or R-22) with the extracting agent such that the agent extracts the solute (R-12 or R-22) from the mixture and forms a separate phase therefrom. This is followed by separating the two immiscible phases of R-12-rich (or R-22-rich) solvent and R-12/R-134a (R-22/R-134a) mixture which now has a correspondingly reduced concentration of the solute (R-12 or R-22).

The separation process may be facilitated by using a stripping agent such as ethylene glycol or triethylene glycol, or a mixture thereof, which are not miscible with mineral oils, and have better miscibility with R-134a than either R-12 or R-22.

DETAILED DESCRIPTION OF THE INVENTION

It has been discovered that efficient total (or partial) separation of R-134a and R-12 (or R-22) can be achieved via liquid-liquid extraction using paraffinic (or naphthalenic) mineral oils as the extraction solvents. To demonstrate the feasibility of the process and to evaluate the parameters for the design of the process and associated equipment, experiments were carried out on various ternary mixtures comprising R-134a, one of the refrigerants R-12 or R-22, and an extraction solvent (i.e., paraffinic and naphthalenic mineral oils, triethylene glycol). Results of these tests are presented in FIGS. 1 through 4. In these figures, the dashed-lines represent the loci of the so-called "cloud points", in which separate one-phase liquid region from the two-phase region. The dotted-lines are tie-lines whose end points give the concentration of the two immiscible liquid phases in equilibrium. The concentration measurements for generating these figures were conducted using GC and precision mass balance.

Figure 1:
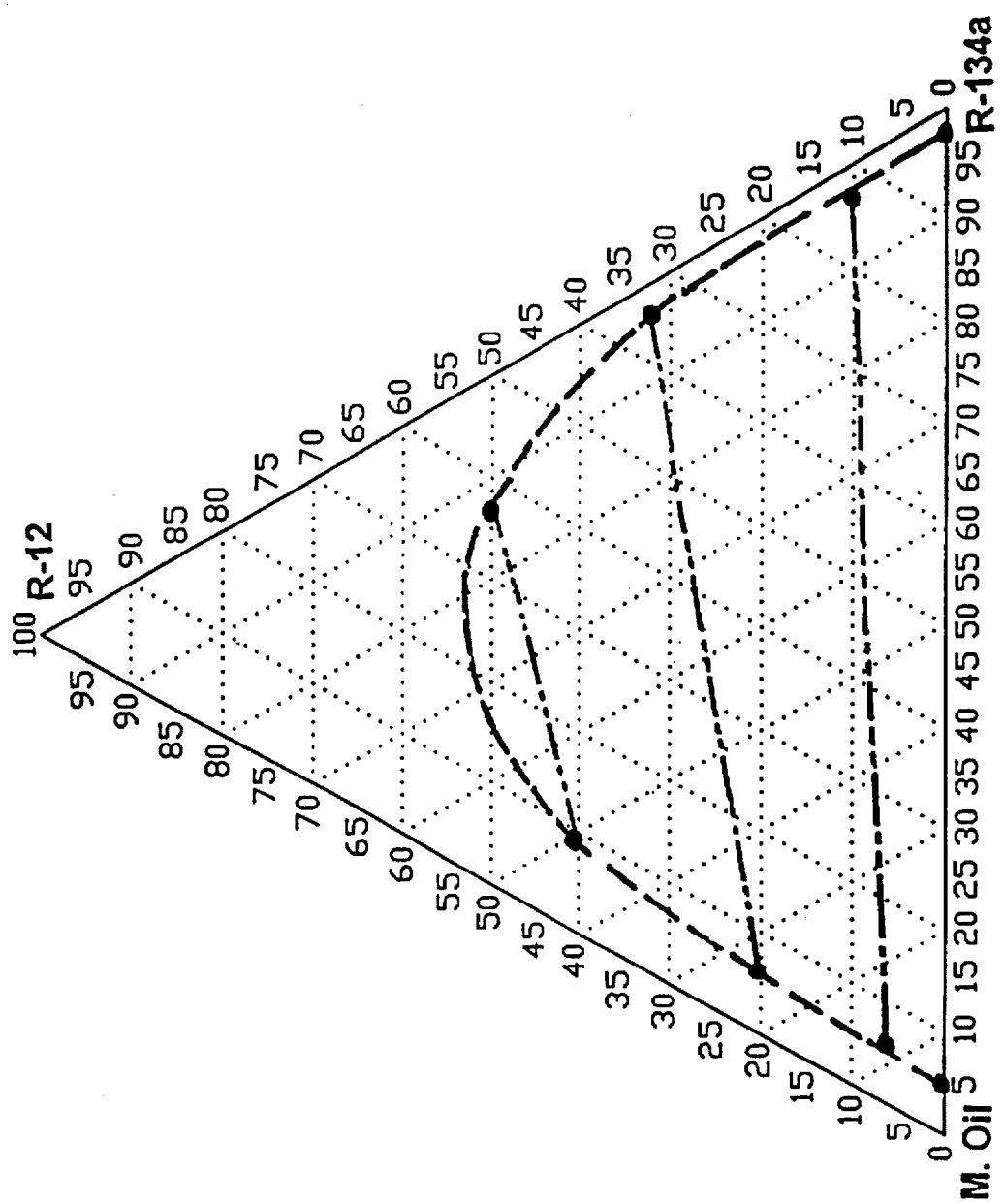
FIG. 1 shows equilibrium data measured at 70° F., for the ternary system of R-12, R-134a and a paraffinic mineral oil (M. Oil).
Figure 2:
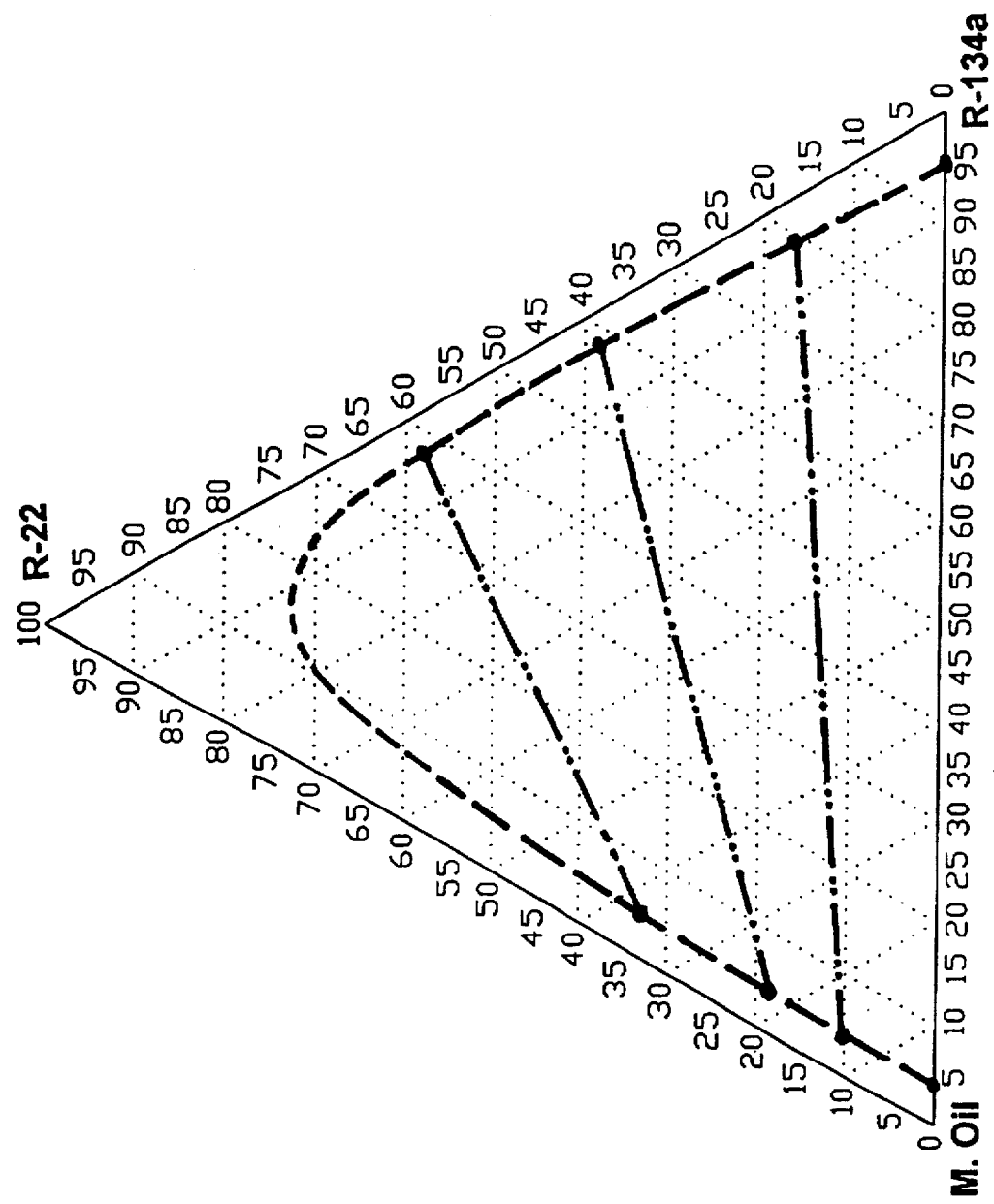
FIG. 2 shows equilibrium data measured at 70° F., for the ternary system of R-22, R-134a and a paraffinic mineral oil (M. Oil).
Figure 3:
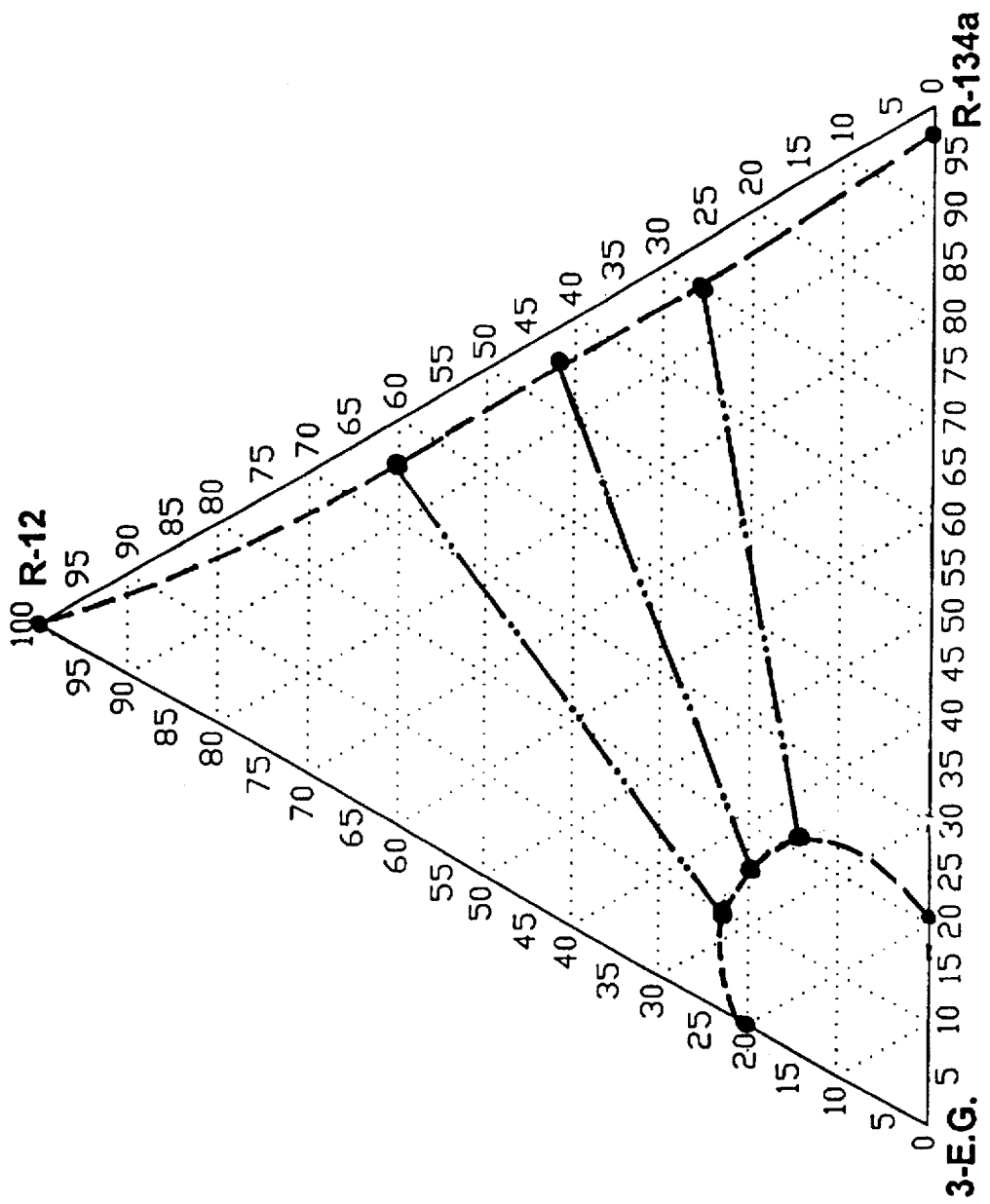
FIG. 3 shows equilibrium data measured at 70° F., for the ternary system of R-12, R-134a and a triethylene glycol (3-E.G.).
Figure 4:
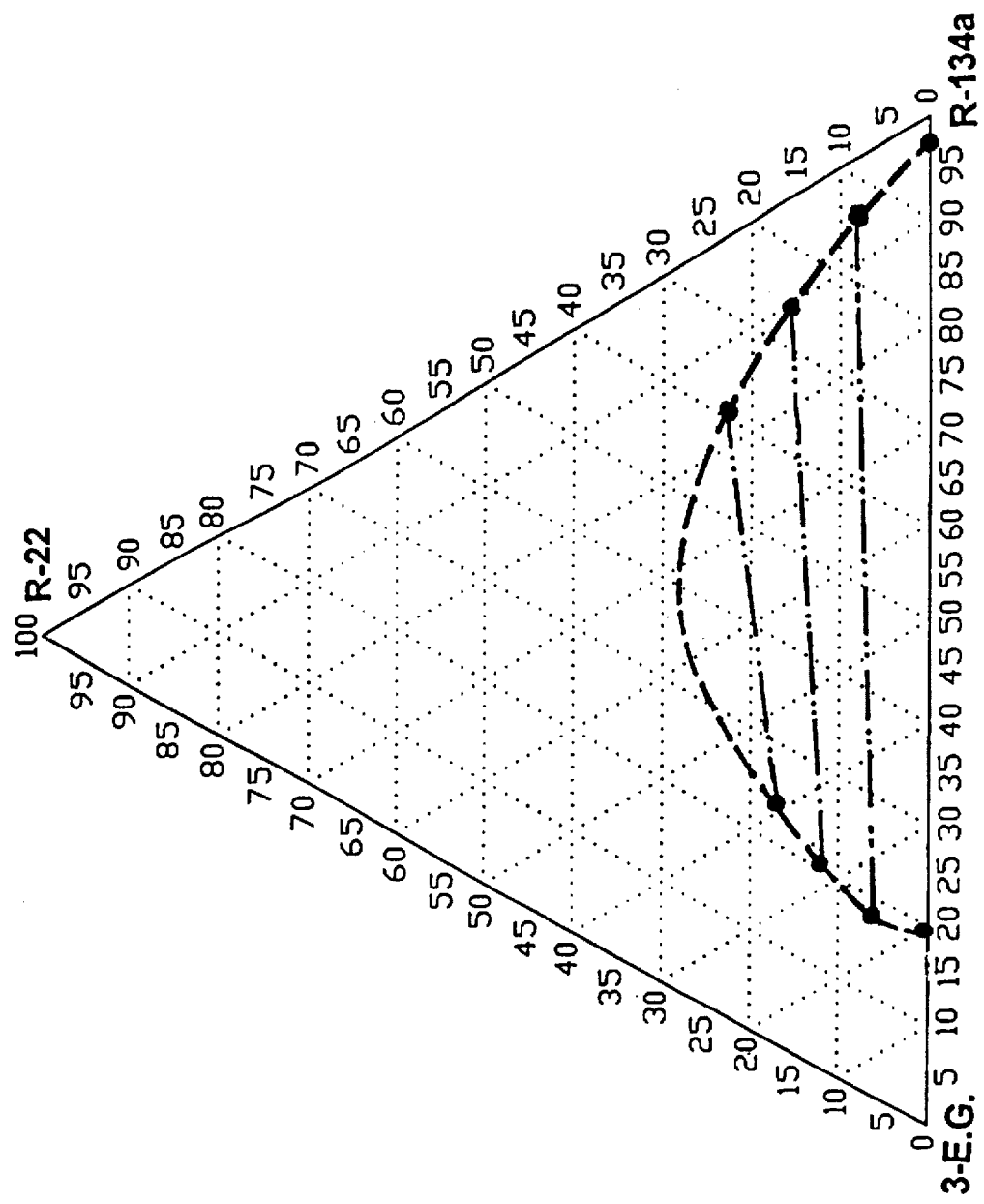
FIG. 4 shows equilibrium data measured at 70° F., for the ternary system of R-22, R-134a and a triethylene glycol (3-E.G.).

FIGS. 1 and 2 show that R-12 and R-22 are completely miscible with the mineral oil whereas the solubility of R-134a in mineral oils (and vise versa) is limited. This makes the mineral oils a good extraction solvent for total or partial separation of R-134a from its mixtures with R-12 or R-22. FIG. 3 shows the equilibrium data measured for the ternary system composed of R-134a, R-12 and triethylene glycol (3-E.G.). This figure reveals that, depending on the composition of the feed mixture, 3-E.G. may be used to extract R-134a and yield (pure or partially pure) R-12. The equilibrium data measured for the ternary system comprising R-134a, R-22, and 3-E.G. are presented in FIG. 4. This figure indicates that, unlike R-12, R-22 is fully miscible with 3-E.G. Therefore, 3-E.G. cannot be used as a stripping agent, but directly and solely as the extraction solvent for the separation of R-134a from R-22. Comparing FIGS. 2 and 4, one concludes that for some range of feed compositions, use of 3-E.G. will yield more pure R-134a (with the same number of contact stages as mineral oil). Feed with compositions richer than about 45% R-22, 3-E.G. is not capable of separating R-134a and R-22 and mineral oil is the better extraction solvent for separating R-134a from R-22, as may be noted in FIG. 2.

From the phase-equilibrium data, the distribution coefficients and separation factors are calculated and presented in Tables 1 through 4 for ternary system containing R-134a, R-12 or R-22, and mineral oil or 3-E.G.

TABLE 1

Equilibrium Data Measured for R-134a, R-12, and Mineral Oil System at 70° F.

| Sample | Component | M.Oil-Rich Phase (Extract Phase) Mass Fraction | R-134a-Rich Phase (Raffinate Phase) Mass Fraction | Distribution Coefficient | Separation Factor | |
|---|---|---|---|---|---|---|
| S1 | R-134a | 0.079 | 0.868 | 10.99 | R-12/R-134a | 0.138 |
|    | R-12   | 0.069 | 0.105 | 1.522 | — | — |
|    | Mineral Oil | 0.852 | 0.027 | 0.0317 | R-12/M. Oil | 48.0 |
| S2 | R-134a | 0.085 | 0.650 | 7.65 | R-12/R-134a | 0.213 |
|    | R-12   | 0.195 | 0.318 | 1.63 | — | — |
|    | Mineral Oil | 0.720 | 0.033 | 0.0458 | R-12/M. Oil | 35.6 |
| S3 | R-134a | 0.090 | 0.325 | 3.61 | R-12/R-134a | 0.396 |
|    | R-12   | 0.396 | 0.565 | 1.43 | — | — |
|    | Mineral Oil | 0.514 | 0.110 | 0.212 | R-12/M. Oil | 6.75 |

Table 1 shows that the separation factors for R-12 by mineral oil are generally much greater than unity (from 6.75 to 48.0), whereas the separation factors for R-12 by R-134a are generally much less than unity (from 0.138 to 0.396). This indicates that mineral oils are a proper extraction solvent for this mixture, and can effectively extract R-12 from its mixtures with R-134a.

TABLE 2

Equilibrium Data Measured for R-134a, R-22, and Mineral Oil System at 70° F.

| Sample | Component | M.Oil-Rich Phase (Extract Phase) Mass Fraction | R-134a-Rich Phase (Raffinate Phase) Mass Fraction | Distribution Coefficient | Separation Factor | |
|---|---|---|---|---|---|---|
| S4 | R-134a | 0.062 | 0.785 | 12.67 | R-22/R-134a | 0.153 |
|    | R-22   | 0.090 | 0.175 | 1.944 | — | — |
|    | Mineral Oil | 0.848 | 0.040 | 0.047 | R-22/M. Oil | 41.4 |
| S5 | R-134a | 0.065 | 0.565 | 8.69 | R-22/R-134a | 0.251 |
|    | R-22   | 0.173 | 0.377 | 2.179 | — | — |
|    | Mineral Oil | 0.762 | 0.058 | 0.076 | R-22/M. Oil | 28.7 |
| S6 | R-134a | 0.069 | 0.374 | 5.42 | R-22/R-134a | 0.334 |
|    | R-22   | 0.311 | 0.562 | 1.810 | — | — |
|    | Mineral Oil | 0.620 | 0.064 | 0.103 | R-22/M. Oil | 17.5 |

Similarly, the separation factors presented in Table 2 reveal that mineral oils can extract R-22 from its mixtures with R-134a very effectively.

TABLE 3

Equilibrium Data Measured for R-134a, R-12, and 3-E.G. System at 70° F.

| Sample | Component | M.Oil-Rich Phase (Extract Phase) Mass Fraction | R-12-Rich Phase (Raffinate Phase) Mass Fraction | Distribution Coefficient | Separation Factor | |
|---|---|---|---|---|---|---|
| S4 | R-134a | 0.215 | 0.696 | 3.24 | — | — |
|    | R-12   | 0.145 | 0.260 | 1.79 | R-134a/R-12 | 1.81 |
|    | 3-E.G. | 0.640 | 0.044 | 0.069 | R-134a/3-E.G. | 46.9 |
| S5 | R-134a | 0.145 | 0.540 | 3.72 | — | — |
|    | R-12   | 0.200 | 0.414 | 2.07 | R-134a/R-12 | 1.80 |
|    | 3-E.G. | 0.653 | 0.046 | 0.071 | R-134a/3-E.G. | 52.4 |
| S6 | R-134a | 0.092 | 0.346 | 3.76 | — | — |
|    | R-12   | 0.226 | 0.604 | 2.67 | R-134a/R-12 | 1.41 |
|    | 3-E.G. | 0.682 | 0.050 | 0.073 | R-134a/3-E.G. | 51.5 |

On the other hand, from the separation factors presented in Table 3 it is inferred that 3-E.G. has good affinity to extract R-134a from its mixtures with R-12 and its use as stripping agent will facilitate the separation and purification of R-134a and R-12.

TABLE 4

Equilibrium Data Measured for R-134a, R-22, and 3-E.G. System at 70° F.

| Sample | Component | M.Oil-Rich Phase (Extract Phase) Mass Fraction | R-22-Rich Phase (Raffinate Phase) Mass Fraction | Distribution Coefficient | Separation Factor | |
|---|---|---|---|---|---|---|
| S7 | R-134a | 0.145 | 0.865 | 5.97 | — | — |
|    | R-22   | 0.077 | 0.085 | 1.10 | R-134a/R-22 | 5.43 |
|    | 3-E.G. | 0.778 | 0.050 | 0.064 | R-134a/3-E.G. | 93.3 |
| S8 | R-134a | 0.205 | 0.735 | 3.59 | — | — |
|    | R-22   | 0.115 | 0.160 | 1.391 | R-134a/R-22 | 4.88 |
|    | 3-E.G. | 0.680 | 0.105 | 0.154 | N-134a/3-E.G. | 23.3 |
| S9 | R-134a | 0.241 | 0.608 | 2.52 | — | — |
|    | R-22   | 0.174 | 0.222 | 1.276 | R-134a/R-22 | 1.97 |
|    | 3-E.G. | 0.585 | 0.170 | 0.291 | R-134a/3-E.G. | 8.66 |

Table 4, however, indicates that while 3-E.G. has better affinity for R-134a than R-22 and may be used to separate some mixtures of these two, it cannot be employed as a stripping agent similar to the case for R-12/R-134a mixtures.

Figure 5:
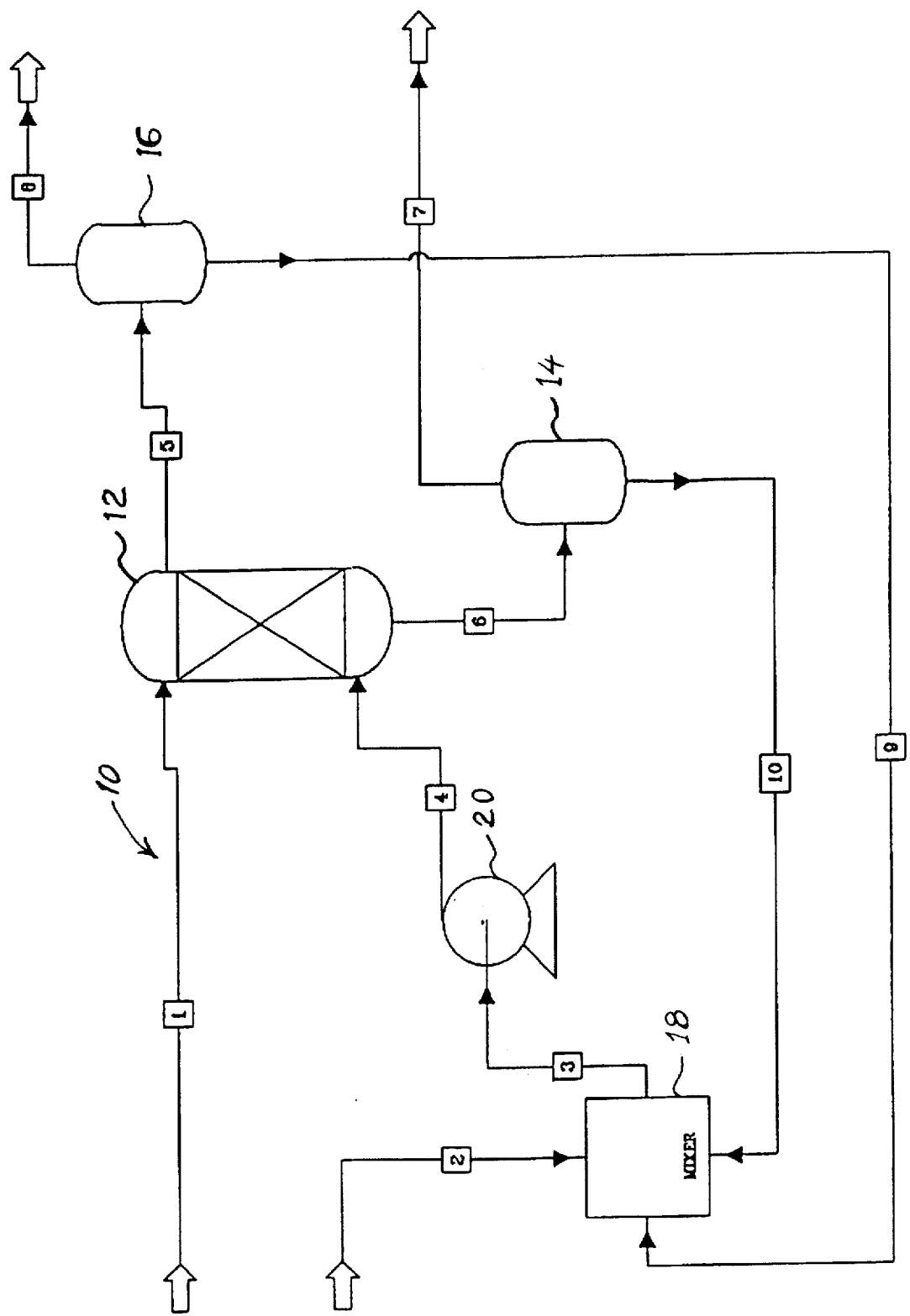
FIG. 5 is a schematic illustration of the liquid-liquid extraction process for separating mixtures of R-134a and R-12 (or R-22) according to the invention.

The separation of the aforementioned refrigerant mixtures can be carried out in a liquid-liquid extractor, indicated generally at 10 as shown in FIG. 5. The extractor may consists of a gravity contactor column 12, two flash drums 14 and 16, and a solvent recovery tank 18. The proper and safe operation of the extractor may require one or two pumps (only one pump 20 is illustrated), several gates, solenoid and pressure relieve valves, which are not illustrated in FIG. 5 for simplicity. The refrigerant mixture feed that is the heavier component (compared to the mineral oil) enters the top of the contactor column 12 through line 1. For purposes of illustration the numerals depicting various lines are inserted with small boxes on the lines. The extraction solvent (mineral oil) which is the lighter component enters the column 12 from the bottom through line 4. Because of the small difference between the densities of mineral oil (0.8 to 0.86 SG) and R-134a (1.23 SG), it is advantageous to employ a mechanically assisted gravity contactor, such as rotating disk contactor (RDC) or Scheibel contactor, in order to generate proper phase dispersion. The raffinate phase is purified (or partially purified) R-134a which is removed from the bottom of the column through line 6. This stream may contain small amount of mineral oil that is easily separated by boil-off in the flash drum 14. Pure (or partially pure) R-134a vapor is removed from the top of the drum 14 through line 7, and the recovered oil is removed from the bottom of the drum and is fed back to the solvent recovery tank 18 through line 10.

The extract phase at the top of the column 12 is the R-12-rich (or R-22-rich) oil phase which is sent through line 5 to the second flash drum 16. From the bottom of this drum 16, the mineral oil is removed and sent to the solvent recovery tank 18 via line 9. The vapor collected at the top of the drum 16 is rich in R-12 (or R-22) which is stored for further purification.

The flow rates of the extraction solvent (through line 4) and the feed stream (line 1), as well as the number of equivalent theoretical stages of the contactor column are independent variables of the process which are selected or controlled to produce the desired purify level of R-134a. Under steady state conditions, the mineral oil make-up to the solvent recovery tank 18, (via line 2), is very small since the mineral oil is mostly removed from the refrigerants and send back to the solvent recovery tank via lines 9 and 10.

Figure 6:
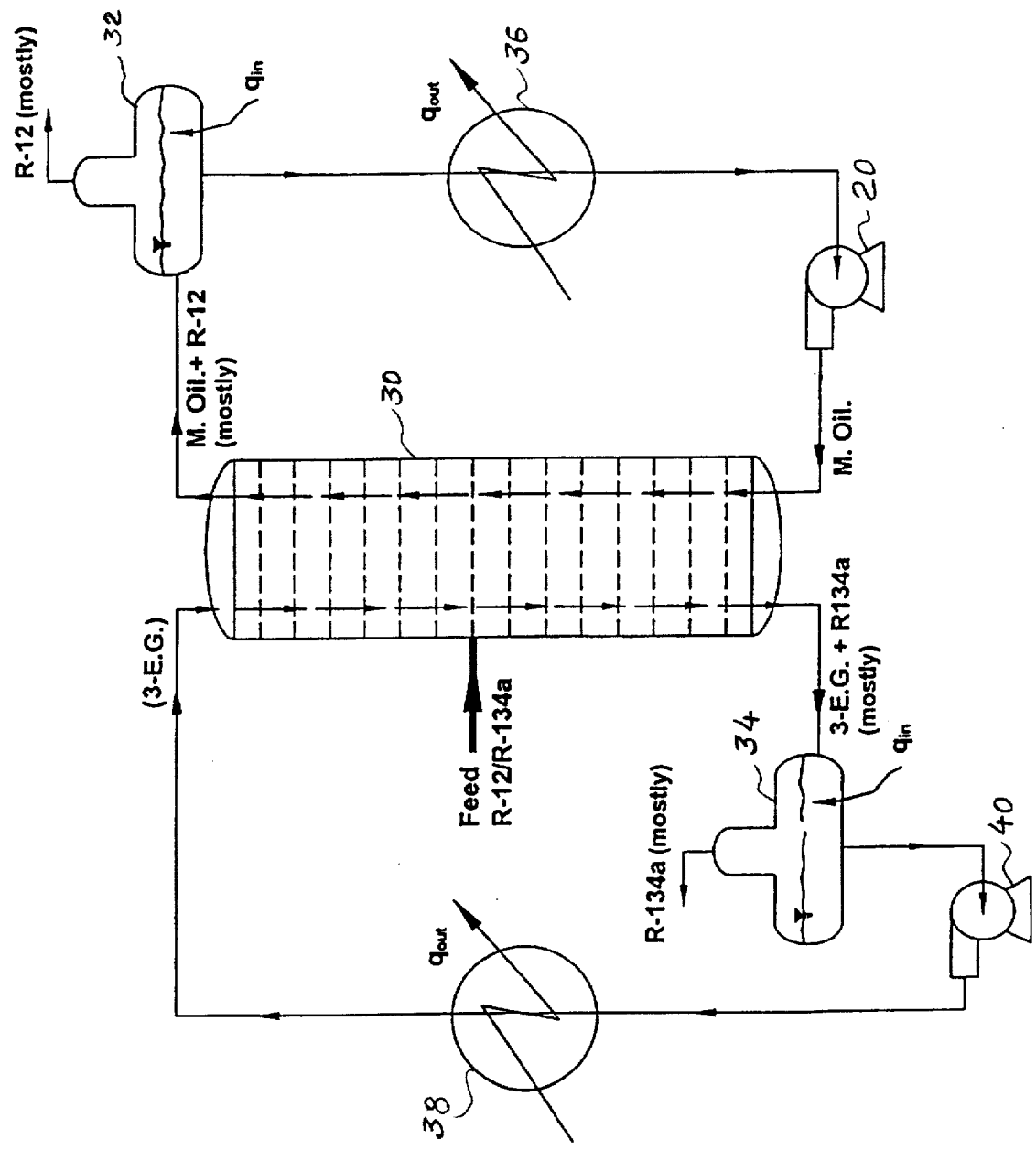
FIG. 6 is a schematic illustration of the liquid-liquid extraction process for separating mixtures of R-134a and R-12 in the presence of two extraction solvents according to the invention.

The process for separation of R-12 from R-134a can be made more efficient by using 3-E.G. as a second extraction solvent (stripping agent), as shown in FIG. 6. This separator consists of a gravity contactor column 30, two flash evaporators 32 and 34, and two coolers 36 and 38 supplied by pumps 20 and 40. For this process, 3-E.G. which has higher density than the mineral oil enters at the top of the contactor column, while the mineral oil enters the column at the bottom, and the refrigerant mixture is fed in the middle of the contactor column. The contactor may be a sieved-plate type (as shown), a rotating disk contactor (RDC), or a Scheibel contactor.

The light mineral oil extracts R-12 from the mixture while flowing upward in the column, and the 3-E.G. extracts R-134a while flow down the column. The two extraction solvents (i.e., mineral oil and 3-E.G.) are totally immiscible with each other, and their densities are different enough to permit phase separation, and counter current flows. From top of the column 30, R-12-rich oil-phase is withdrawn and flashed in the flash drum 32. The mineral oils have significantly higher boiling point than the refrigerants, in general. Therefore, the regeneration of mineral oil (separation from the refrigerants) is simply achieved by boil-off or flashing in flash drum 32. Mineral oil recovered from the bottom of the flash drum 32 is fed back into the column 30 via pump 20.

The heavy 3-E.G. extracts R-134a from the mixture while flowing downward in the column 30. From the bottom of the column 30, R-134a-rich phase is withdrawn and flashed in the second flash drum 34. The 3-E-G. have significantly higher boiling point than the refrigerants, and is easily regenerated by boil-off or flashing in flash drum 34. 3-E.G. recovered from the bottom of the flash drum 34 is fed back into the column 30 via pump 40.

The process according to FIG. 6 may involve simultaneous counter flow of the two solvents. The separation may also be achieved by a controlled cycling of the solvents such that at any given time only one solvent is flowing through the column. In this scheme, in one cycle, 3-E.G. enters from the top in form of droplets in the dispersed phase and flows downward in the mineral oil which is the continuous phase. A period of no flow occurs during which 3-E.G. coalesces to form the continuous phase. For the rest of one cycle, mineral oil enters from the bottom in the form of droplets, which disperse and flow upward in the 3-E.G. By controlling the flow rates of the solvents, and duration of their flow cycle, it is possible to achieve high level of purity for both refrigerant components.

One innovative aspect of this invention is the application of liquid-liquid extraction technique for separation of mixed refrigerants during the reclamation process. Although liquid-liquid extraction technique is well established and frequently used in chemical and pharmaceutical industries, its applicability to separation of any given mixture depends on the finding of an appropriate extraction solvent, and as has been noted in previous art (U.S. Pat. Nos. 4,031,148 and 5,099,082), it is impossible to foresee which extraction agent will render the separation of any two substances feasible.

Therefore, one aspect of this present invention is the surprising discovery that paraffinic or naphthalenic mineral oils render separation of these refrigerant mixtures possible.

Still another innovative aspect of this invention is the finding that ethylene glycol and 3-E.G. may be used as stripping agent to make the separation process more effective and efficient.

Still another innovative aspect of this invention is the application of controlled flow cycling of the two extraction solvents through the contactor column such that the desired levels of purity may be achieved for both refrigerant components.

That which is claimed is:

1. A process for separating R-134a in a mixture with a refrigerant selected from the group consisting of R-12 and R-22 by extracting the R-12 or R-22 by a liquid-liquid extraction using a mineral oil.

2. A process according to claim 1 wherein said mineral oil is selected from the group consisting of a paraffinic or naphthalenic mineral oil.

3. A process according to claim 1 including the step of applying a glycol stripping agent.

4. A process according to claim 1 including flowing the mixture through a gravity column, in a counter flow configuration with the mineral oil.

5. A process according to claim 4 including the step of mechanically agitating the mixture in the gravity column.

6. A process according to claim 5 including the step of flowing the mixture through perforated-plates contained in the gravity column for ensuring droplet generation and phase dispersion.

7. A process according to claim 1 including applying a wash solvent for stripping.

8. A process according to claim 7 wherein said wash solvent is selected from the group consisting of ethylene glycol or 3-E.G.

9. A process for separating R-134a in a mixture with a refrigerant selected from the group consisting of R-12 and R-22 by extracting the R-12 or R-22 by a liquid-liquid extraction through a gravity column using an extraction solvent selected from the group consisting of paraffinic and naphthalenic mineral oils.

10. A process according to claim 9 including operating the gravity column through a controlled cycling mode by introducing, dispersing and removing one extraction solvent selected from the group consisting of paraffinic and naphthalenic mineral oils, coalescing for a predetermined period, and then introducing, dispersing and removing an extraction glycol solvent, then coalescing period of time.

11. A process according to claim 9 including measuring in real time the transient concentrations of an extract and raffinate from the process and adjusting the flow rates through the gravity column based on measured transient concentration.

* * * * *